(12) United States Patent
Shannon et al.

(10) Patent No.: US 7,192,922 B2
(45) Date of Patent: Mar. 20, 2007

(54) METHOD OF TREATING LEFT VENTRICULAR DYSFUNCTION

(75) Inventors: Richard P. Shannon, Sewickley, PA (US); Dariush Elahi, Foxboro, MA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 197 days.

(21) Appl. No.: 10/299,162

(22) Filed: Nov. 19, 2002

(65) Prior Publication Data

US 2004/0097411 A1 May 20, 2004

(51) Int. Cl.
*A61K 38/00* (2006.01)
(52) U.S. Cl. .............................. 514/12; 514/8; 424/1.69
(58) Field of Classification Search .................... 514/12
See application file for complete search history.

(56) References Cited

U.S. PATENT DOCUMENTS

| 6,706,689 | B2* | 3/2004 | Coolidge et al. | 514/12 |
| 2002/0107206 | A1* | 8/2002 | Coolidge et al. | 514/21 |
| 2002/0146405 | A1* | 10/2002 | Coolidge et al. | 424/94.61 |
| 2003/0220255 | A1* | 11/2003 | Knudsen et al. | 514/12 |
| 2004/0002454 | A1* | 1/2004 | Coolidge et al. | 514/12 |
| 2004/0180824 | A1* | 9/2004 | Knudsen | 514/12 |

OTHER PUBLICATIONS

Richard P. Shannon, Disclosure to Mario Ehlers, (Oct. 17, 2000).
L.A. Nikolaidis et al., "Mechanisms Whereby Rapid Ventricular Pacing Causes LV Dysfunction," Abstract, (Mar. 21, 2001).
Lazaros A. Nikolaidis, et al., "GLP-1 Improves Myocardial Performance in Conscious Dogs With Pacing Induced Heart Failure," Abstract, (Mar. 21, 2001).
Lazaros A. Nikolaidis, et al., "Effects of Glucagon-Like Peptide-1 in Patients With Acute Myocardial Infarction and Left Ventricular Dysfunction After Successful Reperfusion," Circulation, p. 962-965, (Mar. 2, 2004).
Lazaros A. Nikolaidis, et al., "Recombinant Glucagon-Like Peptide-1 Increases Myocardial Glucose Uptake and Improves Left Ventricular Performance in Conscious Dogs With Pacing-Induced Dilated Cardiomyopathy," Circulation, p. 955-961, (Aug. 24, 2004).
Hiroshi Yamamoto, et al., "Glucagon-Like Peptide-1 Receptor Stimulation Increases Blood Pressure and Heart Rate and Activates Autonomic Regulatory Neurons," The Journal of Clinical Investigation, vol. 110 (No. 1), p. 43-52, (Jul. 2002).
Martin G. Vila Petroff, et al., "Glucagon-Like Peptide-1 Increases cAMP but Fails to Augment Contraction in Adult Rat Cardiac Myocytes," Circulation Research, p. 445-452, (Aug. 31, 2001).
Lazaros A. Nikolaidis, et al., "Glucagon-Like Peptide-1 Limits Myocardial Stunning after Brief Coronary Occlusion and Reperfusion in Conscious Canines," The Journal of Pharmacology and Experimental Therapeutics, vol. 312 (No. 1), p. 1-6, (2005).
Jose M. Barragan, et al., "Interactions of Exendin-(9-39) with the Effects of Glucagon-Like Peptide-1-(7-36) Amide and of Exendin-4 on Arterial Blood Pressure and Heart Rate in Rats," Regulatory Peptides 67, p. 63-68, (1996).
Jose' Manuel Barragan, et al., "Neural Contribution to the Effect of Glucagon-Like Peptide-1-(7-36) Amide on Arterial Blood Pressure in Rats," The American Physiological Society, p. E784-E791, (1999).
Ewa Bojanowska, et al., "Effects of Centrally or Systemically Injected Glucagon-Like Peptide-1 (7-36) Amide on Release of Neurohypophysial Hormones and Blood Pressure in the Rat," Regulatory Peptides 91, p. 75-81, (2000).
J. M. Barragan, et al., "Changes in Arterial Blood Pressure and Heart Rate Induced by Glucagon-Like Peptide-1-(7-36) Amide in Rats," The American Physiological Society, p. E459-E466, (1994).
Lazaros A. Nikolaidis, et al., "Active Metabolite of GLP-1 Mediates Myocardial Glucose Uptake and Improves Left Ventricular Performance in Conscious Dogs with Dilated Cardiomyopathy," Abstract, p. 1-34.
L.A. Nikolaidis, et al., "Active Metabolite of GLP-1 Mediates Myocardial Glucose Uptake and Improves Left Ventricular Performance in Conscious Dogs with Dilated Cardiomyopathy," Entrez PubMed, p. 1-2, (Jul. 25, 2005).
Lazaros A. Nikolaidis, et al., "Active Metabolite of GLP-1 Mediates Increases Myocardial Glucose Uptake and Improves Hemodynamics in Dilated Cardiomyopathy," Circulation, vol. 110, No. 17, (Oct. 26, 2004).
Lazaros A. Nikolaidis, et al., "Glucagon-Like Peptide-1 (GLP-1) Limits Myocardial Stunning Following Acute Coronary Occlusion and Reperfusion in Conscious Canines," Abstracts, Journal of the American College of Cardiology, (Mar. 6, 2002).
Lazaros A. Nikolaidis, et al., "Safety and Efficacy of GLP-1 in Acute Myocardial Infarction Association with Left Ventricular Systolic Dysfunction," Circulation, vol. 106, No. 19, (Nov. 5, 2002).
Lazaros A. Nikolaidis, et al., "Recombinant Glucagon Like Peptide-1 (rGLP-1) Improves Survival in Spontaneously Hypertensive Heart Failure (SHHF) Rats," Abstracts from Scientific Sessions 2003, Circulation, vol. 108, No. 17, (Oct. 28, 2003).
Indu Poornima, et al., "The Synergistic Effects of Aging and Heart Failure on Myocardial Insulin Signaling in Spontaneously Hypertensive Heart Failure (SHHF) Rats," Abstracts from Scientific Sessions 2003, Circulation, vol. 108, No. 17, (Oct. 28, 2003).

* cited by examiner

*Primary Examiner*—Cecilia J. Tsang
*Assistant Examiner*—Maury Audet
(74) *Attorney, Agent, or Firm*—Ansel M. Schwartz

(57) ABSTRACT

A method of treating a patient having heart failure due to LV systolic dysfunction with an LV ejection fraction less than 40%. The method includes the steps of administering to a patient in need thereof, a compound selected from the group consisting of GIP, GIP analogs, GIP derivatives and pharmaceutically-acceptable salts thereof, GLP-1, GLP-1 analogs, GLP-1 derivatives and pharmaceutically-acceptable salts thereof, at a therapeutically effective amount to improve LV function.

18 Claims, 8 Drawing Sheets

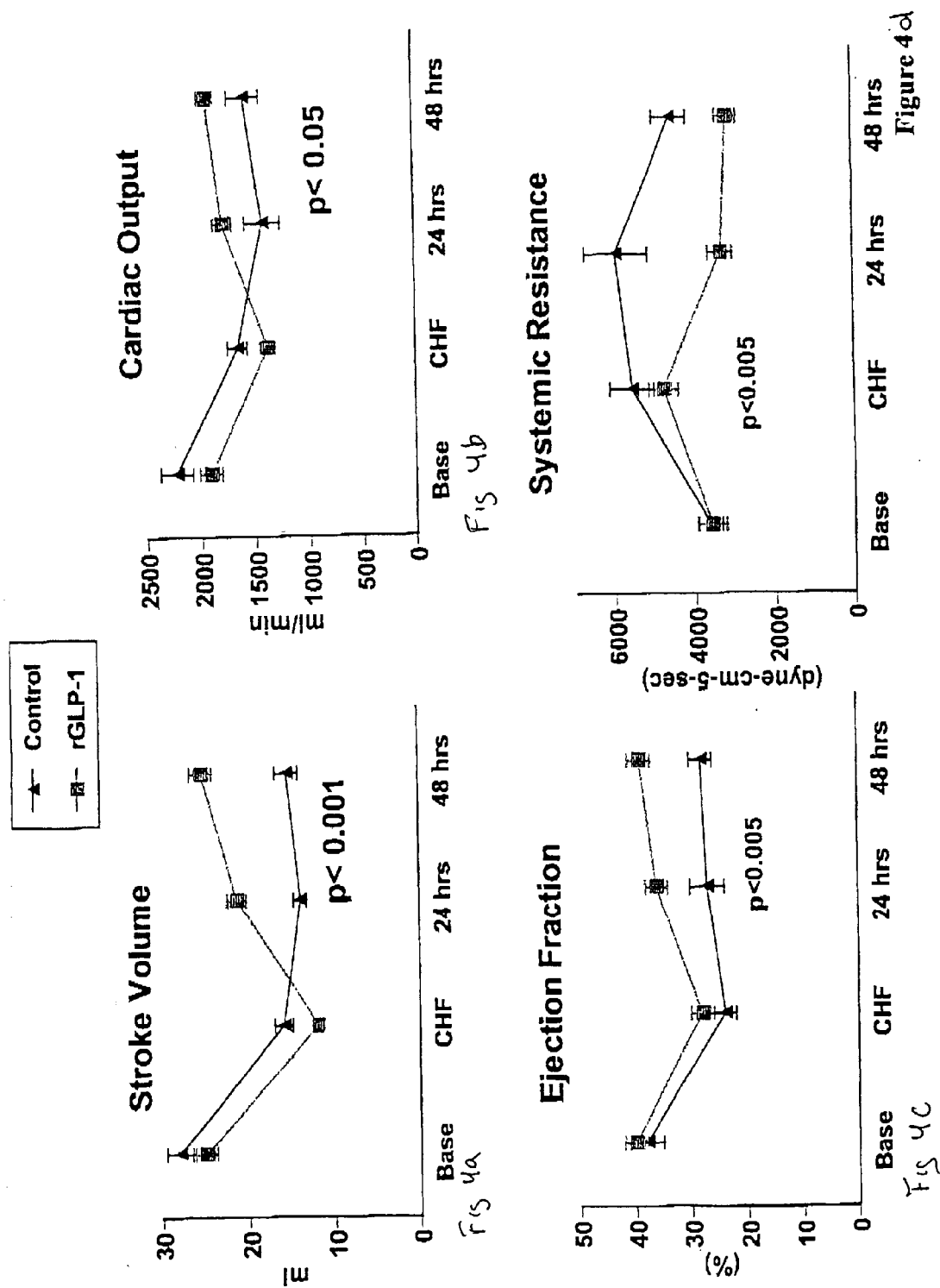

METHOD OF TREATING LEFT VENTRICULAR DYSFUNCTION

FIELD OF THE INVENTION

The present invention is related to the use of natural occurring peptides and their metabolites to increase endogenous insulin release and to decrease glucagon release in states of heart failure, and thereby enhance myocardial glucose uptake. More specifically, the present invention is related to the use of incretins in the treatment of left ventricular systolic dysfunction with an LV ejection fraction less than 40%.

BACKGROUND OF THE INVENTION

Under normal conditions, the heart prefers NEFA as its source of ATP production. It has long been recognized that the acutely injured or chronically failing myocardium has a preference for glucose as its metabolic source for oxidative phosphorylation and ATP production. Davila-Roman V G, Vedala G, Herrero P, et al., "Altered myocardial fatty acid and glucose metabolism in idiopathic dilated cardiomyopathy," *J. Amer. Coll. Cardiol.*, 2002 40:271–277; Paolisso G, Gambardella A, Galzerano D, et al., "Total-body myocardial substrate oxidation in congestive heart failure," *Metabolism*, 1994; 43:174–179; Depre C, Rider M H, Hue L., "Mechanisms of control of heart glycolysis," *Eur. J Biochem.*, 1998;258:277–290, all of which are incorporated by reference herein. This preference is based upon the biochemistry of glucose oxidation in which the complete beta oxidation of mole of glucose is associated with less consumption of oxygen for the amount of ATP produced (3.17 moles ATP/$O_2$ molecule consumed) compared to the complete oxidation of a mole of NEFA (2.83 moles ATP/$O_2$ molecule consumed). Following myocardial injury, the reduced oxygen requirements favor the oxidation of glucose. Furthermore, this shift in metabolic preference is mediated by changes in the molecular expression of rate limiting steps in both NEFA and glucose oxidation [Razeghi P, Young M E, Alcorn J L, et al., "Metabolic gene expression in fetal and failing human heart," *Circulation*, 2001; 104:2923–2931, incorporated by reference herein], attesting to its evolutionary advantage.

As heart failure progresses from a compensated to a decompensated state, there is a reduction in creatine phosphate and eventual depletion of high energy phosphate stores. Shen W, Asai K, Uechi M, et al., Ingwall J S, "Progressive loss of myocardial ATP due to a loss of total purines during the development of heart failure in dogs," *Circulation*, 1999; 100: 2113–2118, incorporated by reference herein. The depletion of the heart's required source of energy leads to further contractile dysfunction and hemodynamic decompensation that characterizes the advanced stages of heart failure. It has been observed that the failing heart in its advanced stage becomes resistant to the action of insulin, and, therefore, demonstrates reduced glucose uptake and oxidation. This occurs at a time when the failing heart capacity for using alternate substrates (NEFA) has been modified at a transcriptional level. Razeghi P, Young M E, Alcorn J L, et al., "Metabolic gene expression in fetal and failing human heart," *Circulation*, 2001; 104:2923–2931, incorporated by reference herein. Taken together, these factors lead to a state of further energy deprivation, ATP depletion, and progressive heart failure.

GLP-1 (7–36 amide) or GLP-1 (7–39) are peptides produced by the L cells in the ileum. Drucker D J, "Biological actions and therapeutic potential of the glucagons-like peptides," *Gastroenterology*, 2002; 122:531–44, incorporated by reference herein. It is one of three peptides (GLP-1, GLP-2, and GIP) from the glucagon-secretion family, that have been indicated in the control of appetite and satiety. These pro-glucagon derived peptides are secreted in response to nutrient ingestion, and GLP-1 and GIP act as incretins to stimulate insulin secretion. Importantly, these two peptides are glucose dependent and the insulinotropic action is attenuated at plasma glucose levels of less than 4 mmol/L. Therefore, GLP-1 stimulated insulin release is carefully controlled in an autocrine fashion, minimizing the risks of hypoglycemia that are associated with exogenous insulin administration. In addition, GLP-1 and its analogues have insulin-independent actions, including the inhibition of gastric emptying, reduction of food ingestion, beta islet cell hypertrophy, and, importantly, the inhibition of glucagon. GLP-1 is rapidly degraded by dipeptidase IV to a 9–36 peptide that also stimulates glucose uptake in insulin independent fashion. Thus, the purpose of the present invention is preferably to take advantage of the unique properties of GLP-1 to facilitate myocardial glucose uptake and oxidation in heart failure—a newly recognized insulin resistant state in which the heart is critically dependent upon glucose metabolism.

The unique property of GLP-1 to stimulate both insulin release in the presence of hyperglycemia and to suppress glucagon release has a favorable synergistic effect on myocardial glucose metabolism. Glucose uptake by the normally working heart is critically dependent on insulin mediated translocation of the Glut-4 transporter from cytosolic to the membrane compartment. Full activation of the insulin signaling cascade is a prerequisite for this important translocation. Once glucose is taken up into the cell, it may be either oxidized to generate ATP or stored as glycogen to serve as a readily available source of glucose in times of stress. However, most glucose undergoes oxidative metabolism through glycolysis and then enters the tricarboxylic acid cycle (TCA), where it is oxidized to acetyl-COA. The reducing elements generated in the TCA cycle then enter the electron transport chain, where ATP is generated. Insulin receptor stimulation is a prerequisite for both the uptake of glucose by the heart, and for the complete oxidation of glucose through aerobic glycolysis, through the phosphorylation of rate limiting enzymes. Shulman G I, "Cellular mechanisms of insulin resistance," *J. Clin. Invest.*, 2000; 106;171–175, incorporated by reference herein.

Glucagon is a potent counter regulatory hormone to the action of insulin. Glucagon is released by the alpha-islet cells of the pancreas and increases circulating glucose by simulating glycogenolysis and gluconeogenesis through conventional $\beta_2$ adrenergic receptor-cyclic AMP dependent mechanisms. Glucagon is responsible for the recruitment of carnitine and for the activation of CPT-1, a key rate limiting step in the trans-mitochondrial transfer of acetyl-CoA that is critical in the oxidation of non-esterified fatty acids. Glucagon also stimulates NEFA oxidation by inhibiting acyl-CoA carboxylate and thereby reducing concentrations of malonyl CoA. Therefore, glucagon favors fatty acid uptake and oxidation by the heart-limiting glucose oxidation, whereas insulin favor glucose uptake and oxidation by the heart.

By taking advantage of its unique properties, GLP-1 (7–36 amide) or its rapidly cleaved metabolite, GLP-1 (9–36 amide) favorably influences both glucose uptake through its insulinotropic and insulinomimetic mechanisms, at the same time suppressing glucagon, and, therefore, free fatty acid oxidation. The same is true for GIP.

Glucagon-like peptide-1 (GLP-1) has been studied extensively in the treatment of Type II diabetes, largely considered to be an insulin resistant state, in which pancreatic insulin reserves are reduced. Mauvais-Jarvis F, Andreelli F, Hanaire-Broutin H, Charbonnel B, Girard J., "Therapeutic perspectives for type 2 diabetes mellitus: molecular and clinical insights," *Diabetes Metab.*, 2001 Sep.; 27 (4 Pt 1):415–23, incorporated by reference herein. The efficacy in ameliorating the diabetes management is well established. Furthermore, GLP-1 has been shown to be safe and effective in both young and elderly Type II diabetics. DeLeon M J, Chandurkar V, Albert S G, Mooradian A D. "Glucagon-like peptide-1 response to acarbose in elderly type 2 diabetic subjects", *Diabetes Res. Clin. Pract.*, 2002 May; 56 (2): 101–6, incorporated by reference herein; Meneilly et al., "Effect of Glucagon-Like Peptide-1 on Non-Insulin Mediated Glucose Uptake in the Elderly Patient with Diabetes," *Diabetes Care*, 2001; 24:1951–56, incorporated by reference herein; Maneilly et al., "Glucagon-Like Peptide-1 (7–37) Augments Insulin Mediated Glucose Uptake in Elderly Patients with Diabetes," *J. Serentol. Med. Sci.*, 2001: 56A; M6815, incorporated by reference herein. GLP-1 is rapidly metabolized to the 9–36 amino acid, which is ultimately excreted by the kidney. Therefore, the action of GLP-1 is prolonged in the presence of renal insufficiency.

GLP-1, its derivatives, analogs and pharmaceutically-acceptable salts thereof has also been used during the treatment of patients with acute heart attacks. The present invention is directed for use in heart failure, which is a chronic consequence of not only heart attacks, but hypertension, valvular disease and other CV conditions. See U.S. Pat. No. 6,277,819, incorporated by reference herein, by Efendic. This patent deals with acute treatment during a heart attack while the present invention treats the patient chronically, who has LV dysfunction.

SUMMARY OF THE INVENTION

The present invention pertains to a method of treating a patient having heart failure due to LV systolic dysfunction with an LV ejection fraction less than 40%. The method comprises the steps of administering to a patient in need thereof, a compound selected from the group consisting of GIP, GIP analogs, GIP derivatives and pharmaceutically-acceptable salts thereof, GLP-1, GLP-1 analogs, GLP-1 derivatives and pharmaceutically-acceptable salts thereof, at a therapeutically effective amount to improve LV function.

BRIEF DESCRIPTION OF THE DRAWINGS

In the accompanying drawings, the preferred embodiment of the invention and preferred methods of practicing the invention are illustrated in which:

FIGS. 4a–4d show the effects of rGLP-1 on cardiac output, stroke volume, LV ejection fraction, systemic vascular resistance in conscious dogs with advanced DCM compared to saline control.

DETAILED DESCRIPTION

Figure 1:
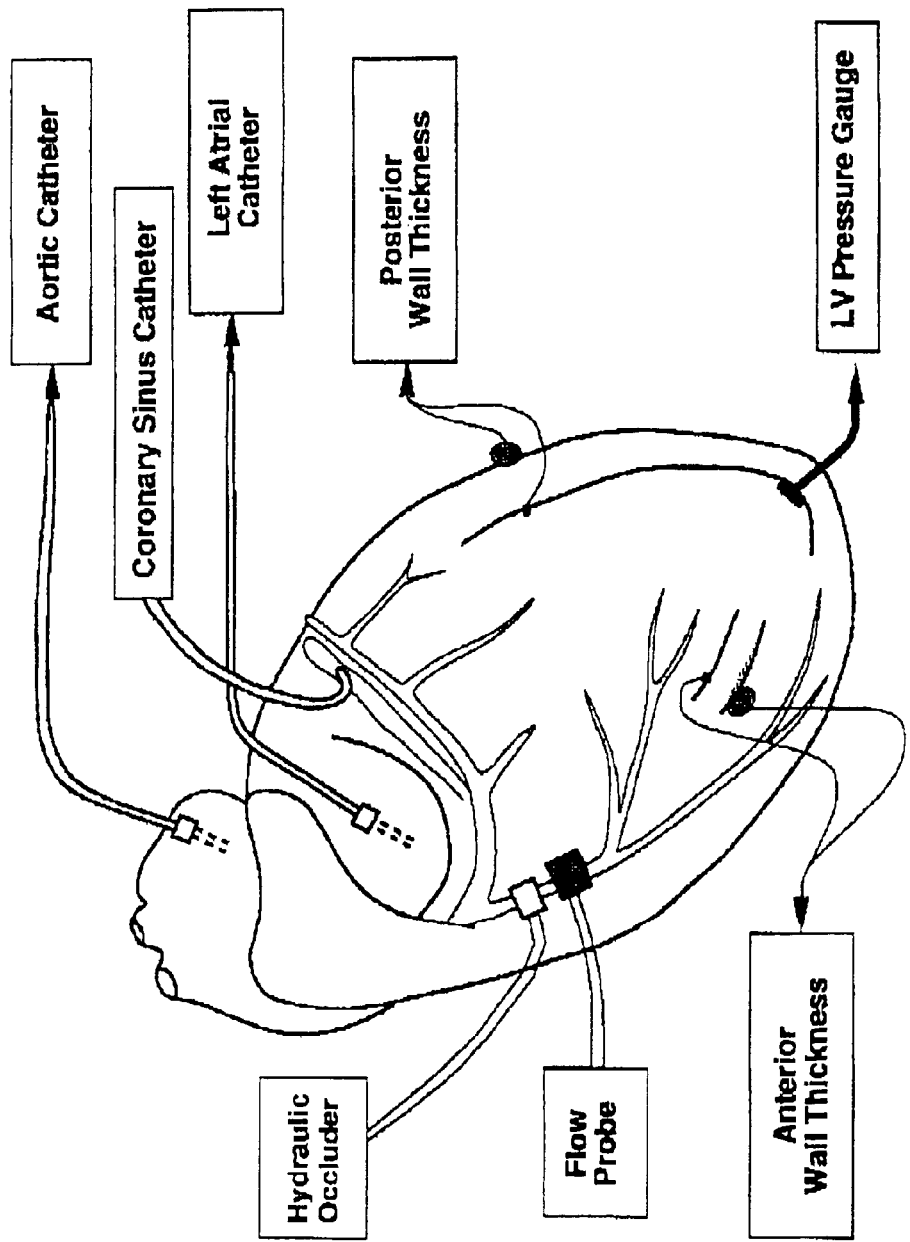
FIG. 1 is a schematic illustration of the instrumentation used in the measurements of the effects of rGLP-1 in conscious, chronically instrumented dogs.

The present invention pertains to a method of treating a patient having heart failure due to LV systolic dysfunction with an LV ejection fraction less than 40%. The method comprises the steps of administering to a patient in need thereof, a compound selected from the group consisting of GIP, GIP analogs, GIP derivatives and pharmaceutically-acceptable salts thereof, GLP-1, GLP-1 analogs, GLP-1 derivatives and pharmaceutically-acceptable salts thereof, GLP-1, GLP-1 analogs, GLP-1 derivatives and pharmaceutically-acceptable salts thereof, at a therapeutically effective amount to improve LV function. GLP-1, GLP-1 analogs, GLP-1 derivatives and pharmaceutically-acceptable salts thereof are listed in U.S. Pat. No. 6,277,819, incorporated by reference herein. Additionally, see Anderson, N H et al., "Medium Dependent of the Secondary Structure of Exendin-4 and Glucagon Like Peptide-1," *Bioorg. Med. Chem.*, 2002; 10:79–85, incorporated by reference herein; and Luque, M A et al., "Glucagon Like Peptide-1 (GLP-1) and Glucose Metabolism in Human Myocytes," *J. Endocrinol.*, 2002; 173:465–473, incorporated by reference herein.

Preferably, the compound is administered intravenously. The administration is preferably continuous. Preferably, the rate of administration of the compound is between 1 and 20 pmol/kg/min. Even more preferably, the rate of administration of the compound is between 1 and 2.5 pmol/kg/min. Preferably, the continuous administration is between 1 day and 12 weeks.

Alternatively, the intravenous administration is intermittent. Preferably, the intermittent administration occurs for between 1 day and 12 weeks. Alternatively, the compound is administered intravenously and also administered by another parenteral route. The other parenteral route is preferably the subcutaneous route. Alternatively, the compound is only administered subcutaneously.

In a preferred embodiment, the compound administered is GLP(7–36) amide (the naturally occurring peptide that binds to a distinct GLP-1 receptor), or a pharmaceutically-acceptable salt thereof. In another preferred embodiment, the compound administered is GLP(9–36) amino acid metabolite, or a pharmaceutically-acceptable salt thereof. In yet another preferred embodiment, the compound administered is the GLP-1 receptor agonist, exendin-4, or a pharmaceutically-acceptable salt thereof. In another preferred embodiment, the compound administered is GIP, and their metabolites, such as GIP (1–42) or GIP (3–42) or pharmaceutically-acceptable salts thereof.

Preferably, the improved LV function is an improvement in New York Heart Association Class, incorporated by reference herein. In addition, or separately, the improved LV function is preferably an improvement in hemodynamics which include reductions in LV diastolic pressures, reductions in pulmonary artery pressures, increases in cardiac output and declines in heart rate. In addition, or separately, the improved LV function is preferably a greater than 5% increase in LV ejection fraction.

In the operation of the invention, GLP-1 receptors have been identified by immuno-histochemical techniques in the myocardium of rats and humans. Wei, Y, Mojsov, S., "Distribution of GLP-1 and PACAP receptors in human tissues," *Acta. Physiol. Scand.*, 1996;157:355–357, incorporated by reference herein. The role of these myocardial receptors has, heretofore, not been fully appreciated. Recent experiments using excendin-4 in rats have demonstrated that subcutaneous or intra-ventricular administration of excendin 4 is associated with hypertension and tachycardia in restrained rats. Yamamoto, H, Lee, C E, Marcus, J N, Williams, T D, Overton, J M, Lopez, M E, Hollenberg, A N, Baggio, L, Saper, C B, Drucker, D J, Elmquist, J K, "Glucagon-like peptide-1 receptor stimulation increases blood pressure and heart rate and activates autonomic regulatory neurons," *J. Clin. Invest.*, 2002 Jul.; 110 (1):43–52, incorporated by reference herein. These effects have been demonstrated to be mediated through increased sympathetic nervous system activation. In contrast, GLP-1 (7–36 amide) had no effect on myocyte contractility in rat cardiomyocytes, in vitro, despite increases in cAMP. Vila Petroff, M G, Eagan, J M, Wang, X, Sollott, S J, "Glucagon-like peptide-1 increases camp but fails to augment contraction in adult rat cardiac myocytes," *Circ. Res.*, 2001;89:445–452, incorporated by reference herein. However, there are no previous data demonstrating the effect of GLP-1 on resting hemodynamics in heart failure, nor are there any other data demonstrating the effects of GLP-1 on glucose metabolism in heart failure.

Figure 2:
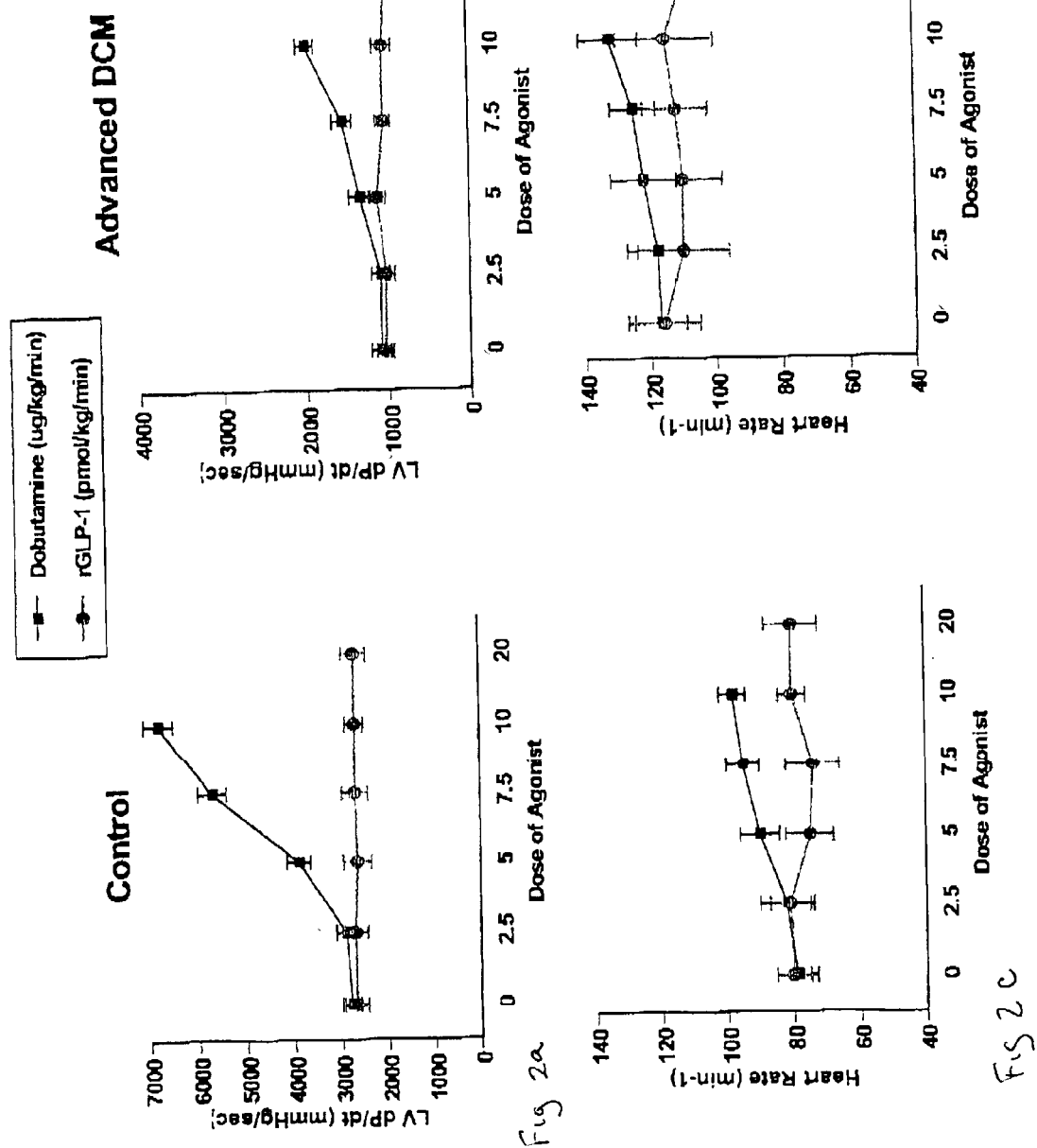
FIGS. 2a–2d show the dose response to rGLP-1 in normal conscious dogs and conscious dogs with advanced DCM compared to the response to the sympathomimetic, dobutamine. There were no acute hemodynamic effects of rGLP-1 while dobutamine had the expected effects.

FIG. 1 illustrates characteristic instrumentation of conscious, chronically instrumented dogs studied in the laboratory. Under sterile surgical technique, the animals are instrumented as indicated and allowed to recover fully from their surgery. At the time, they are taught to lie quietly on the experimental table before study. To determine if acute GLP-1 (7–36 amide) infusion is associated with hemodynamic effects in conscious chronically instrumented dogs, graded infusions for ten minutes at doses of 1.25, 2.5, 5, 10 and 20 pmol/kg/min in six normal dogs and in six dogs with advanced dilated cardiomyopathy were studied. The response of the graded infusion to the classic iontopic agent, Dobutamine, (2.5, 5, 7.5, 10 and 15 µ/kg/min.) was compared. GLP-1 had no significant, dose related effects on left ventricular pressure, left ventricular dP/dt, cardiac output, or heart rate (FIG. 2). This is in contrast to the synthetic $B_1$ agonist, Dobutamine, which demonstrated predictable effects in normal dogs and de-sensitized effects in heart failure as has been published previously. Nikolaidis, L A, Hentosz, T, Doverspike, A, et al., "Catecholamine stimulation is associated with impaired myocardial $O_2$ utilization in heart failure," *Cardiovas. Res.*, 2002;53:392–404, incorporated by reference herein.

Figure 3:
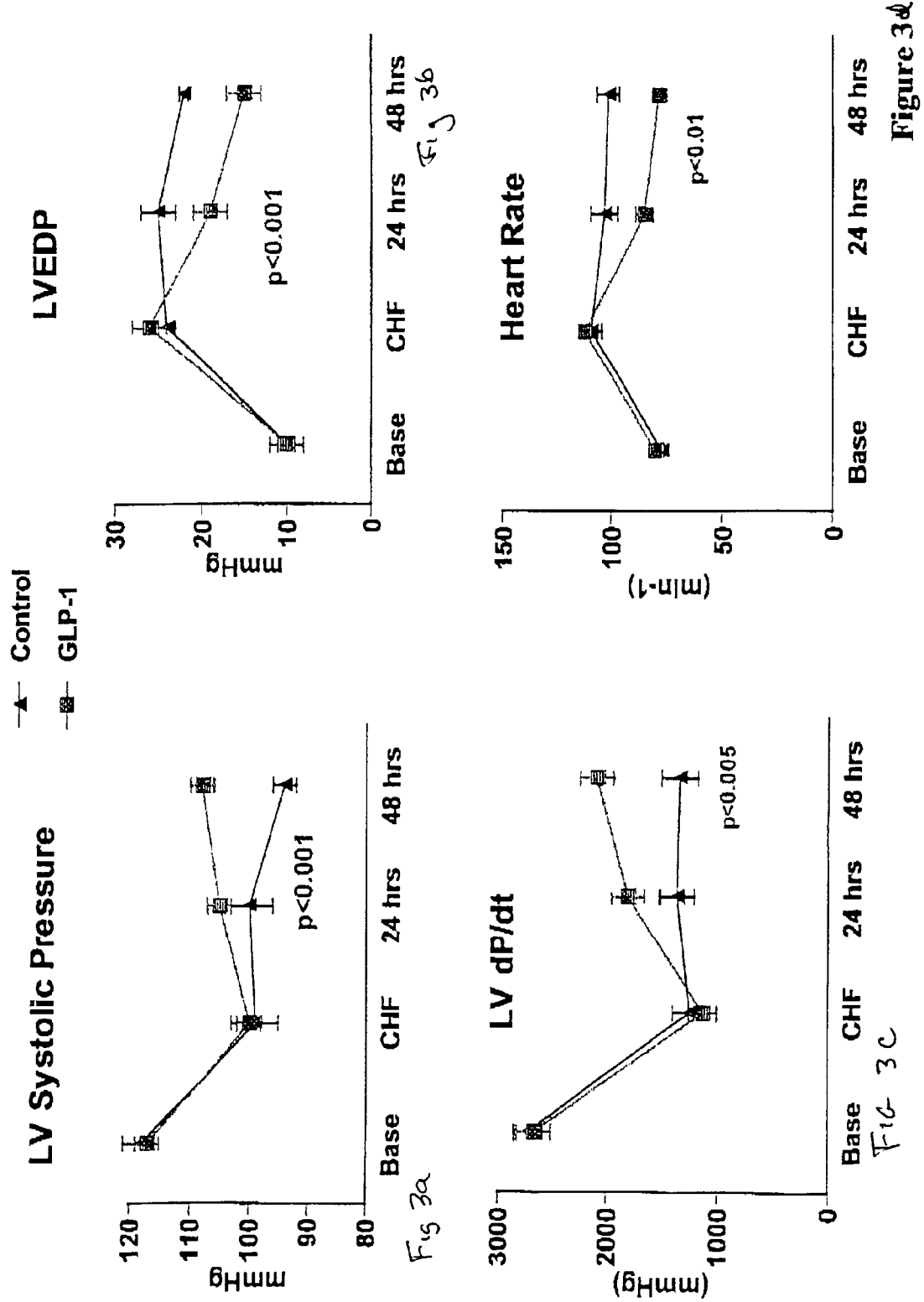
FIGS. 3a–3d show the effects of r GLP-1 on LV systolic pressure, LV end diastolic pressure, LV dP/dt, and heart rate in conscious dogs with advanced DCM compared to saline control.
Figures 5A, 5B:
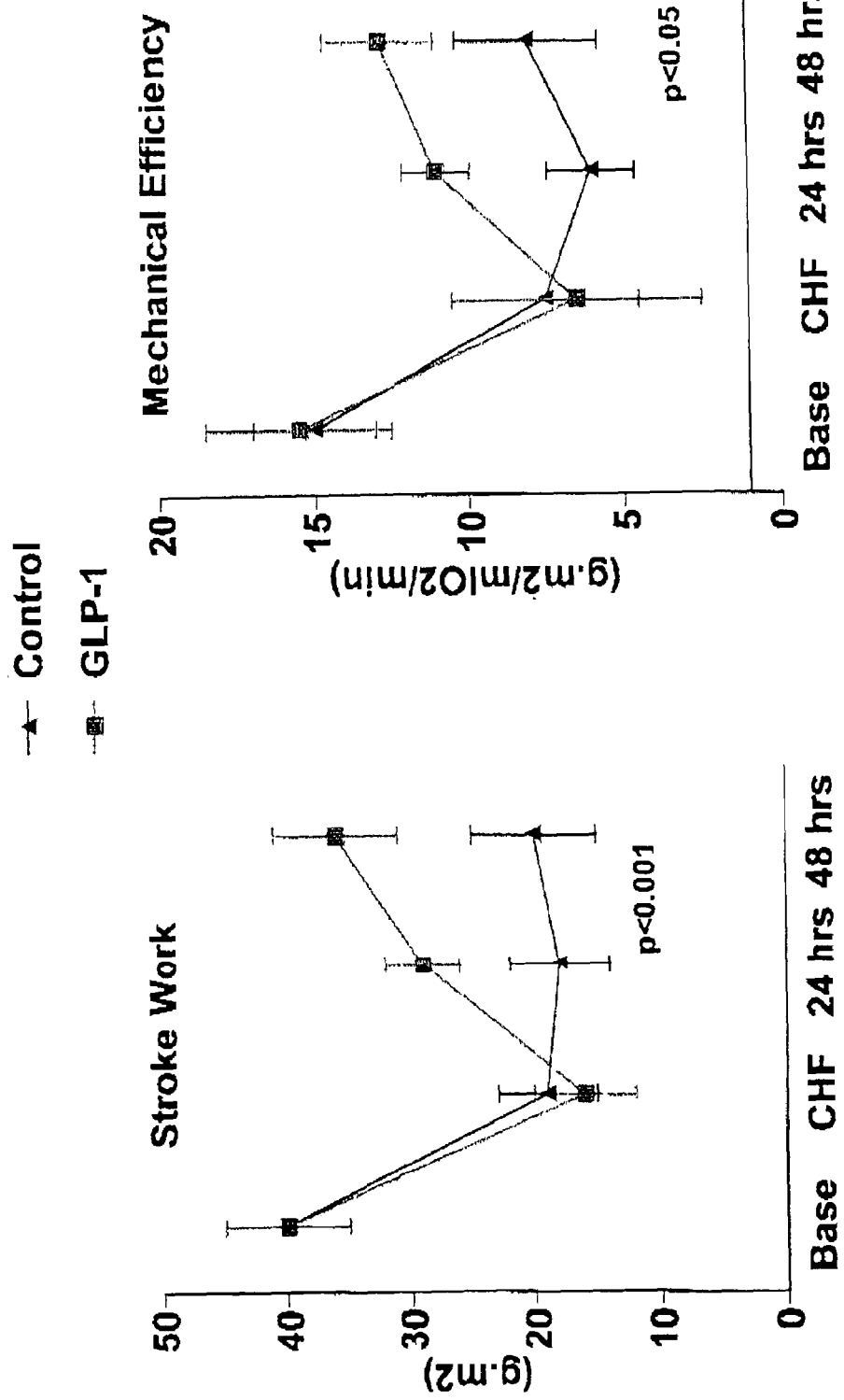
FIGS. 5a and 5b show the effects of rGLP-1 on stroke work and LV external efficiency in conscious dogs with advanced DCM compared to saline control.
Figures 6A, 6B:
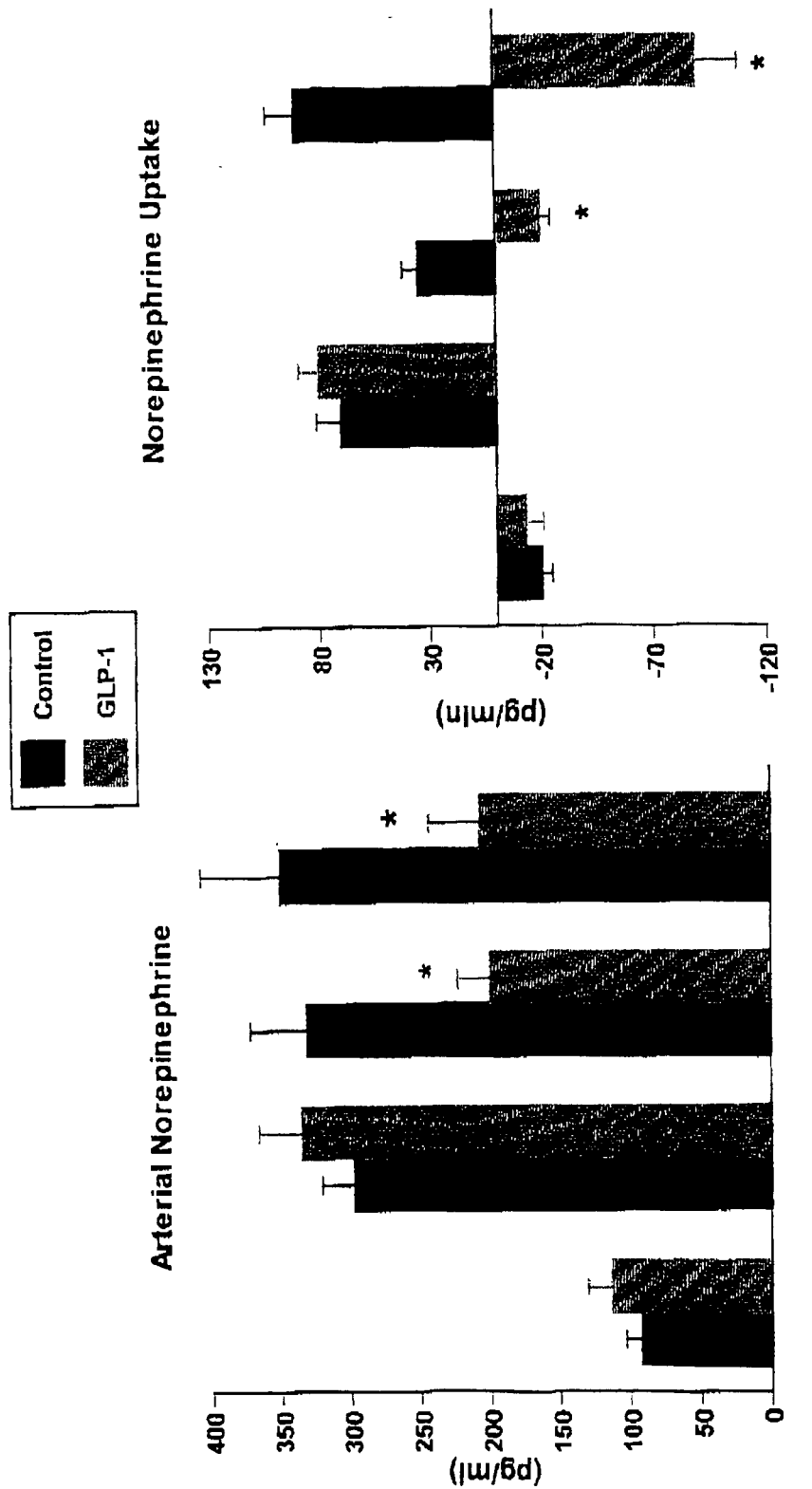
FIGS. 6a and 6b show the effects of rGLP-1 on transmyocardial norepinephrine uptake as a reflection of sympathetic drive to the myocardium in conscious dogs with advanced DCM compared to saline controls.
Figures 7A, 7B:
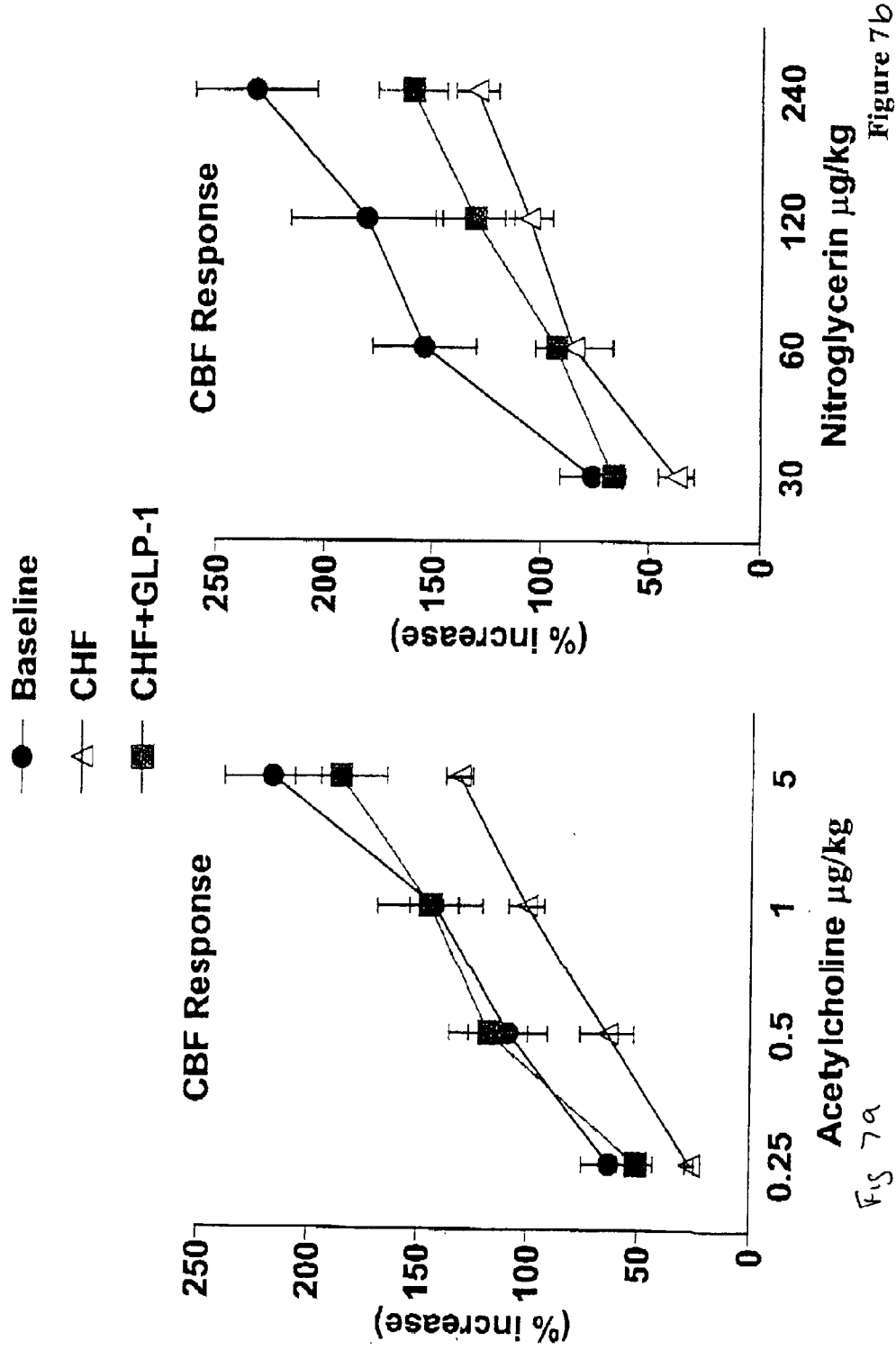
FIGS. 7a and 7b show the effects of rGLP-1 on endothelial dependent coronary vasodilation in conscious dogs. Advanced DCM was associated with impaired coronary flow responses to acetylcholine. These responses were restored following 48-hour infusion of rGLP-1. The response to the non-endothelial dependent vasodilator, nitroglycerin was unaffected.

A 48 hour continuous intravenous infusion of GLP-1 (7–36 amide), (1.5 pmol/kg/min) in five normal dogs to determine the hemodynamic effect of chronic infusion in the absence of dilated cardiomyopathy was conducted. There were no significant hemodynamic effects associated with the continuous infusion in normal animals. FIGS. 3–5 illustrates the effects of GLP-1 (7–36 amide) infusion (1.5 pmol/kg/min) intravenously for 48 hours in 20 conscious, chronically instrumented animals with advanced heart failure. These effects have been compared to similarly instrumented animals with advanced heart failure that received a control saline infusion of equal volume (3 nl/day) illustrate the hemodynamic effects of chronic GLP-1 infusion in advanced DCM. GLP-1 (7–36 amide) infusion was associated with a restoration of left ventricular pressure, improvement in contractility, improvement in cardiac output, and reduction in heart rate and LVEDP. FIG. 6 reveals that GLP-1 infusion, compared to saline, was associated with suppression of myocardial sympathetic activity. GLP-1 was associated with restoration of endothelial dependent vaso dilatation response to acetylcholine (FIG. 7). Table 1 shows the effects of rGLP-1 on metabolic parameters in saline controls compared to rGLP-1 treated group. Myocardial glucose uptake was enhanced following rGLP-1 in association with a significant increase in the ratio of insulin (pmol/L) to glucagon (pg/ml), consistent with the known biological activity of GLP-1. GLP-1 had little effect on increased plasma insulin levels in the setting of euglycemia. However, GLP-1 was effective in reducing plasma glucagon levels, thereby, improving the ratio of insulin to glucagon. This resulted in improved myocardial uptake of glucose in advanced DCM, compared to substrate preference in the control group.

TABLE 1

The Effects of GLP-1 on Myocardial Substrate Uptake

| | Control (n = 6) | | | | GLP-1 (n = 9) | | | |
|---|---|---|---|---|---|---|---|---|
| | Baseline | CHF | 24 hrs | 48 hrs | Baseline | CHF | 24 hrs | 48 hrs |
| NEFA (µmol/min) | 6.23 ± 0.83 | 4.97 ± 0.71 | 4.81 ± 0.43 | 5.12 ± 0.16 | 5.23 ± 0.83 | 3.17 ± 0.61* | 4.53 ± 0.58 | 5.16 ± 0.73** |
| Glucose (µmol/min) | 5.23 ± 0.71 | 3.13 ± 0.61* | 3.31 ± 0.27 | 3.56 ± 0.21 | 6.67 ± 1.22 | 3.44 ± 0.81* | 8.72 ± 1.05** | 7.00 ± 0.94** |
| Lactate (µmol/min) | 4.16 ± 0.61 | 2.07 ± 1.01* | 2.18 ± 0.51 | 2.98 ± 0.76 | 4.78 ± 1.04 | 2.64 ± 0.91* | 3.61 ± 0.62 | 4.04 ± 0.74** |
| Insulin/ Glucagon | 1.5 ± 0.25 | 1.98 ± 0.36 | | 2.05 ± 0.32 | 1.36 ± 0.21 | 1.79 ± 0.29 | | 3.12 ± 0.24** |
| NE (pmol/min) | 42.4 ± 6.7 | 26.0 ± 2.3* | 23.4 ± 2.7* | 29.3 ± 4.3* | 30.9 ± 4.8 | 18.7 ± 3.6 | 26.3 ± 3.1 | 30.5 ± 4.9** |

Figure 8:
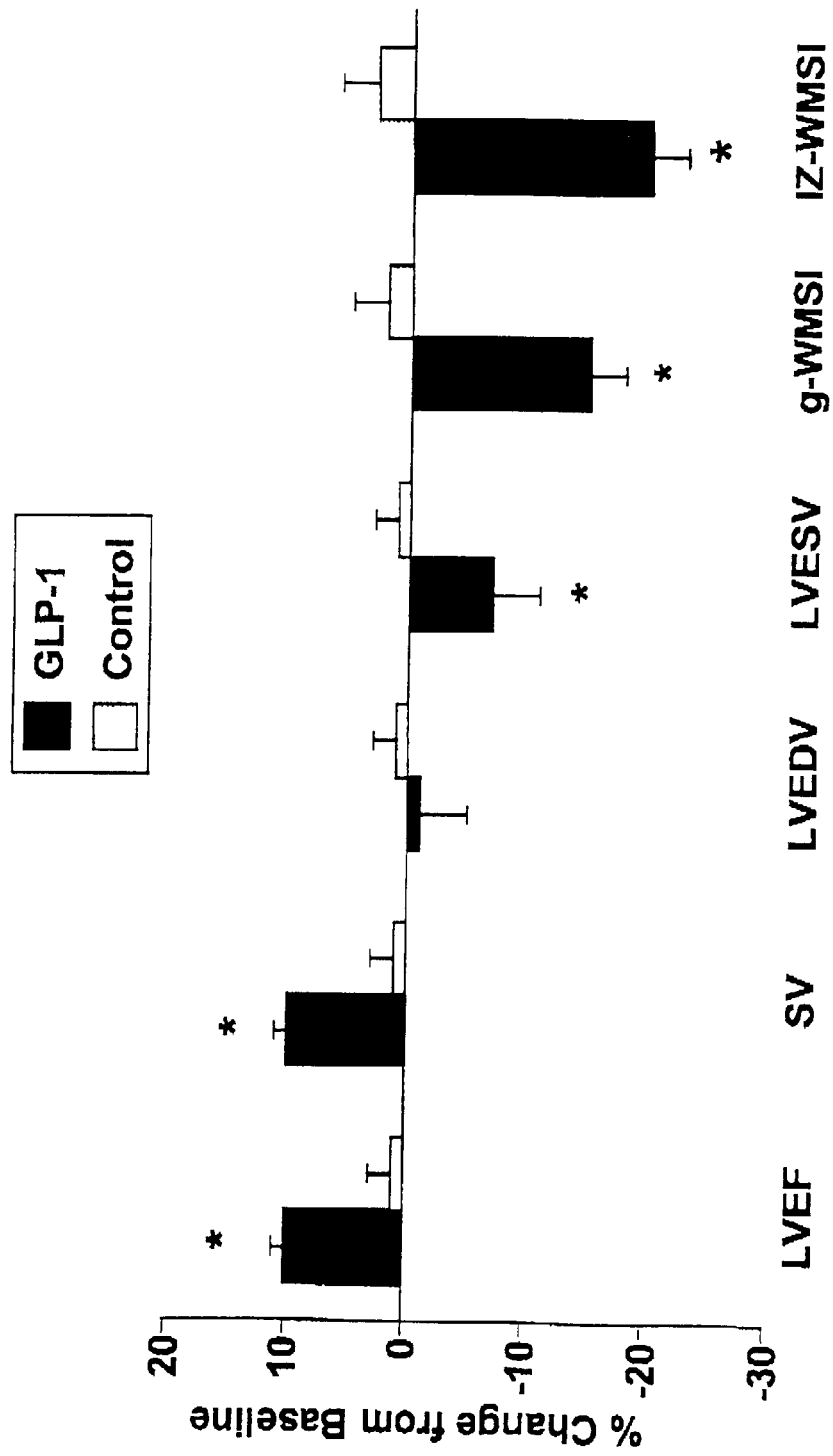
FIG. 8 shows the effects of rGLP-1 on regional and global LV systolic performance following large MI.

The effects of continuous intravenous infusion of GLP-1 (1.5 pmol/kg/min) intravenously for 72 hours was studied in ten adults presenting with severe acute myocardial infarction. These were compared to eleven adults with similar large myocardial infarction (LVEF<35%) all of whom underwent percutaneous coronary intervention and subsequently were treated for 72 hours thereafter. FIG. 8 reveals the overall improvement in left ventricular hemodynamics seen in the GLP-1 treated group compared to patient receiving standard care. These data demonstrate that GLP-1 was associated with an improvement in left ventricular function in patients presenting with large myocardial infarctions and global and regional left ventricular systolic abnormalities.

These data provide existing evidence to support the utility of the incretin, GLP-1 (7–36 amide) or its metabolites (GLP-1 9–36 amide) and its derivatives and analogs in the treatment of left ventricular systolic dysfunction in both dilated cardiomyopathy and ischemic induced left ventricular dysfunction.

The higher insulin levels seen following oral versus intravenous administration of glucose at the same glycemic levels are mediated by hormone(s) released from the gut. This is known as incretin effect. There are two naturally occurring hormones and both are glucose-dependant in that they are more potent as the glycemic level increases. The two hormones are glucose-dependent insulinotropic polypeptide (GIP) and glucagon-like peptide (GLP-1). Both peptides have been infused into normal subjects and patients with type 2 diabetes; Elahi D, McAloon-Dyke M, Fukagawa N K, Meneilly G S, Sclater A L, Minaker K L, Habener J F, Andersen D K: The insulinotropic actions of glucose-dependent insulinotropic polypeptide (GIP) and glucagon-like peptide-1 (7–37) in normal and diabetic subjects. Regulatory Peptides 51:63–74,1994, incorporated by reference herein. In normal subjects during euglycemia GLP-1 is insulinotropic which GIP is not. During hyperglycemia (10.4 mmol/l, 187 mg/dl) GIP (2.0 pmol·kg–1·min–1) increased plasma insulin levels to ~900 pmol/l (150 µU/ml). In control experiments in which only hyperglycemia is established, the insulin levels are ~280 pmol/l (47 µU/ml). GLP-1 (1.5 pmol·kg–1·min–1), on the other hand, increased insulin levels to ~2000 pmol/l (333 µU/ml). Furthermore, when both peptides are infused, the insulinotropic effects of the hormones are additive (~2800 pmol/l, 467 µU/ml). Thus, this study demonstrates that both hormones are potent incretins, that GLP-1 is more potent than GIP and that the effects of the two hormones are additive with respect to their insulinotropic action. Both hormones are rapidly cleaved by dipeptidyl peptidase IV within 30–120 seconds. It has also been demonstrated that B-cell sensitivity to second-generation sulfonylurea is increased (2 fold) when GIP is administered; Meneilly G, Bryer-Ash M, Elahi D: The effect of glyburide on beta-cell sensitivity to glucose-dependent insulinotropic polypeptide. Diabetes Care 16:110–114,1993, incorporated by reference herein. The insulinomimetic effects of GIP are similar to the established insulinomimetic effects of GLP1; Meneilly G, Bryer-Ash M, Elahi D: The effect of glyburide on beta-cell sensitivity to glucose-dependent insulinotropic polypeptide. Diabetes Care 16:110–114,1993, incorporated by reference herein. A large part of the insulinomimetic effects of both peptides are due to the cleaved product of these two hormones when the two amino acids are removed by dipeptidyl peptidase IV.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for treating a human patient with heart failure due to left ventricular (LV) systolic dysfunction with an LV ejection fraction less than 40% comprising administering for 72 hours or more to said human patient, a compound selected from the group consisting of GIP, GIP analogs, GIP derivatives and pharmaceutically-acceptable salts thereof, GLP-1, GLP-1analogs, GLP-1 derivatives and pharmaceutically-acceptable salts thereof, at a rate of administration of the compound of between 1 and 20 pmol/kg/min to improve the following LV functions:

LV ejection fraction (LVEF); stroke volume (SV); LV end-systolic volume (LVESV); global wall motion score index (g-WMSI); and infarct zone wall motion score index (IZ-WMSI).

2. The method of claim 1 wherein the compound is administered intravenously.

3. The method of claim 2 wherein the administration is continuous.

4. The method of claim 3 wherein the rate of administration of the compound is between 1 and 2.5 pmol/kg/min.

5. The method of claim 3 wherein the continuous administration is between 3 days and 12 weeks.

6. The method of claim 2 wherein the intravenous administration is intermittent.

7. The method of claim 6 wherein the intermittent administration occurs for between 3 days and 12 weeks.

8. The method of claim 2 wherein the compound is administered intravenously and also administered by another parenteral route.

9. The method of claim 8 wherein the other parenteral route is the subcutaneous route.

10. The method of claim 1 wherein the compound is administered subcutaneously.

11. The method of claim 1 wherein the compound administered is GLP(7–36) amide, or a pharmaceutically-acceptable salt thereof.

12. The method of claim 1 wherein the compound administered is GLP(9–36) amino acid metabolite, or a pharmaceutically-acceptable salt thereof.

13. The method of claim 1 wherein the compound administered is, or a pharmaceutically-acceptable salt thereof.

14. The method of claim 1 wherein the improved LV function is an improvement in New York Heart Association Class.

15. The method of claim 1 wherein tile improved LV function is an improvement in hemodynamics which include reductions in LV diastolic pressures, reductions in pulmonary artery pressures, increases in cardiac output and declines in heart rate.

16. The method of claim 1 wherein the improved LV function results in a greater than 5% increase in LV ejection fraction.

17. The method of claim 11 wherein the compound administered is GIP(1–42) amide, or a pharmaceutically-acceptable salt thereof.

18. The method of claim 11 wherein the compound administered is GIP(3–42) amide, or a pharmaceutically-acceptable salt thereof.

* * * * *